(12) United States Patent
Hughes

(10) Patent No.: US 7,383,946 B2
(45) Date of Patent: Jun. 10, 2008

(54) MATERIALS FOR STORING AND RELEASING REACTIVE GASES

(76) Inventor: Kenneth D. Hughes, 765 Bellemeade Pl., Alpharetta, GA (US) 30004

( * ) Notice: Subject to any disclaimer, the term of this patent is extended or adjusted under 35 U.S.C. 154(b) by 243 days.

(21) Appl. No.: 11/089,678

(22) Filed: Mar. 25, 2005
(Under 37 CFR 1.47)

(65) Prior Publication Data

US 2005/0235830 A1    Oct. 27, 2005

Related U.S. Application Data

(60) Provisional application No. 60/557,146, filed on Mar. 26, 2004.

(51) Int. Cl.
  *C01B 11/02* (2006.01)
  *B01J 20/26* (2006.01)

(52) U.S. Cl. .................................. 206/0.7; 210/660

(58) Field of Classification Search ............ 95/90, 95/132; 96/108; 210/660, 668, 679; 206/0.6, 206/0.7; 222/3; 252/181.1, 60; 205/556; 204/278

See application file for complete search history.

(56) References Cited

U.S. PATENT DOCUMENTS

| 286,370 A | 10/1883 | Baker |
|---|---|---|
| 3,238,056 A | 3/1966 | Pall et al. |
| 3,344,061 A | 9/1967 | Kellum |
| 3,375,933 A | 4/1968 | Rodman |
| 3,442,796 A | 5/1969 | Hayes |
| 3,545,622 A | 12/1970 | Sakhonvsky |
| 3,662,893 A | 5/1972 | Humbert |
| 3,871,881 A | 3/1975 | Mikelsons |
| 3,996,131 A | 12/1976 | Conn |
| 4,078,112 A | 3/1978 | Bibeau |
| 4,079,001 A | 3/1978 | Haase et al. |
| 4,084,747 A | 4/1978 | Alliger |
| 4,098,690 A | 7/1978 | Semmens |
| 4,160,727 A | 7/1979 | Harris |
| 4,167,479 A | 9/1979 | Besik |
| 4,178,361 A | 12/1979 | Cohen et al. |
| 4,182,676 A | 1/1980 | Casolo |
| 4,190,576 A | 2/1980 | Thomson et al. |
| 4,194,040 A | 3/1980 | Breton et al. |
| 4,198,296 A | 4/1980 | Doumas et al. |

(Continued)

FOREIGN PATENT DOCUMENTS

FR    2790767 A1    9/2000

(Continued)

*Primary Examiner*—Frank M. Lawrence
(74) *Attorney, Agent, or Firm*—Sutherland Asbill & Brennan LLP

(57) ABSTRACT

Compositions, methods, and devices are provided for use in containing and releasing a gas, particularly a reactive gas. The composition can include a reactive gas, reactive gas precursor, or combination thereof; a fluid in which the reactive gas, reactive gas precursor, or combination thereof is dissolved; and a solid material (e.g., particles or fibers) in which fluid is absorbed or adsorbed, wherein the solid material controls the formation or release of the reactive gas. The materials and methods allow rapid and safe generation, transfer, and application of high concentrations of chlorine dioxide gas in solid, liquid, and gas phase systems and are suitable for a variety of chlorine dioxide applications, such as disinfecting and sanitizing liquids, solid surfaces, and porous materials.

12 Claims, 3 Drawing Sheets

U.S. PATENT DOCUMENTS

| | | | |
|---|---|---|---|
| 4,230,595 A | 10/1980 | Yamaji et al. | |
| 4,251,224 A * | 2/1981 | Cowley et al. | 423/477 |
| 4,252,571 A | 2/1981 | Reilly | |
| 4,282,094 A | 8/1981 | Mitchell | |
| 4,330,531 A | 5/1982 | Alliger | |
| 4,482,459 A | 11/1984 | Shiver | |
| 4,585,482 A | 4/1986 | Tice et al. | |
| 4,610,790 A | 9/1986 | Reti et al. | |
| 4,623,467 A | 11/1986 | Hamlin | |
| 4,629,464 A | 12/1986 | Takata et al. | |
| 4,642,192 A | 2/1987 | Heskett | |
| 4,643,182 A | 2/1987 | Klein | |
| 4,645,503 A | 2/1987 | Lin et al. | |
| 4,645,604 A | 2/1987 | Martinola et al. | |
| 4,670,150 A | 6/1987 | Hsiung et al. | |
| 4,683,039 A | 7/1987 | Twardowski et al. | |
| 4,702,836 A | 10/1987 | Mutoh et al. | |
| 4,711,723 A | 12/1987 | Bray | |
| 4,717,566 A | 1/1988 | Eckenhoff et al. | |
| 4,806,244 A | 2/1989 | Guilhem | |
| 4,851,122 A | 7/1989 | Stanley | |
| 4,865,733 A | 9/1989 | Tsuru et al. | |
| 4,874,511 A | 10/1989 | Kawasaki et al. | |
| 4,880,541 A | 11/1989 | Chiron et al. | |
| 4,889,630 A | 12/1989 | Reinhardt et al. | |
| 4,900,444 A | 2/1990 | Seita et al. | |
| 4,902,427 A | 2/1990 | Szczepanik | |
| 4,946,603 A | 8/1990 | Laugharn et al. | |
| 4,988,440 A | 1/1991 | Bernard et al. | |
| 5,019,311 A | 5/1991 | Koslow | |
| 5,071,610 A | 12/1991 | Hagen et al. | |
| 5,082,568 A | 1/1992 | Holler | |
| 5,085,781 A | 2/1992 | Tsuru et al. | |
| 5,089,119 A | 2/1992 | Day et al. | |
| 5,116,415 A | 5/1992 | Rinehart | |
| 5,118,655 A | 6/1992 | Pedersen | |
| 5,122,274 A | 6/1992 | Heskett | |
| 5,126,070 A * | 6/1992 | Leifheit et al. | 252/186.36 |
| 5,127,411 A | 7/1992 | Schoolman et al. | |
| 5,135,654 A | 8/1992 | Heskett | |
| 5,143,752 A | 9/1992 | Nakajima et al. | |
| 5,147,722 A | 9/1992 | Koslow | |
| 5,149,437 A | 9/1992 | Wilkinson et al. | |
| 5,156,739 A | 10/1992 | Dawson et al. | |
| 5,161,686 A | 11/1992 | Weber et al. | |
| 5,180,491 A | 1/1993 | Polasky | |
| 5,189,092 A | 2/1993 | Koslow | |
| 5,198,118 A | 3/1993 | Heskett | |
| 5,205,928 A | 4/1993 | Inove et al. | |
| 5,215,657 A | 6/1993 | Goldfield et al. | |
| 5,238,574 A | 8/1993 | Kawashima et al. | |
| 5,249,948 A | 10/1993 | Koslow | |
| 5,266,203 A | 11/1993 | Mukhopadhyay et al. | |
| 5,271,848 A | 12/1993 | Smith et al. | |
| 5,298,205 A | 3/1994 | Hayes et al. | |
| 5,331,037 A | 7/1994 | Koslow | |
| 5,338,766 A | 8/1994 | Phan et al. | |
| 5,346,565 A | 9/1994 | White | |
| 5,360,609 A * | 11/1994 | Wellinghoff | 514/772.3 |
| 5,384,047 A | 1/1995 | Scheckler et al. | |
| 5,415,759 A | 5/1995 | Cawlfield et al. | |
| 5,422,340 A | 6/1995 | Ammann et al. | |
| 5,482,773 A | 1/1996 | Bair | |
| RE35,267 E | 6/1996 | Tsuru et al. | |
| 5,552,046 A | 9/1996 | Johnston et al. | |
| 5,580,749 A | 12/1996 | Hughes | |
| 5,589,066 A | 12/1996 | Gray | |
| 5,597,487 A | 1/1997 | Vogel et al. | |
| 5,635,071 A | 6/1997 | Al-Samadi | |
| 5,650,446 A | 7/1997 | Wellinghoff et al. | |
| 5,651,884 A | 7/1997 | Ichitsuka et al. | |
| 5,656,140 A | 8/1997 | Oesterle et al. | |
| 5,670,053 A | 9/1997 | Collentro et al. | |
| 5,676,745 A | 10/1997 | Kelly et al. | |
| 5,681,447 A | 10/1997 | Maycock et al. | |
| 5,688,378 A | 11/1997 | Khoe et al. | |
| 5,728,157 A | 3/1998 | Prescott | |
| 5,750,026 A | 5/1998 | Gadkaree et al. | |
| 5,755,969 A | 5/1998 | Okamoto | |
| 5,770,416 A | 6/1998 | Lihme et al. | |
| 5,792,513 A | 8/1998 | Koslow et al. | |
| 5,866,003 A | 2/1999 | Okubo et al. | |
| 5,882,517 A | 3/1999 | Chen et al. | |
| 5,935,887 A | 8/1999 | Sudo et al. | |
| 5,961,843 A | 10/1999 | Hayakawa et al. | |
| 5,977,003 A | 11/1999 | Wilshaw et al. | |
| 5,997,829 A | 12/1999 | Sekine et al. | |
| 6,051,135 A * | 4/2000 | Lee et al. | 210/192 |
| 6,054,050 A | 4/2000 | Dyke | |
| 6,054,059 A | 4/2000 | Latimer, Jr. et al. | |
| 6,103,125 A | 8/2000 | Kuepper | |
| 6,110,375 A | 8/2000 | Bacchus et al. | |
| 6,117,333 A | 9/2000 | Frankiewicz et al. | |
| 6,156,186 A | 12/2000 | Mueller et al. | |
| 6,162,361 A | 12/2000 | Adiga | |
| 6,180,016 B1 | 1/2001 | Johnston et al. | |
| 6,187,192 B1 | 2/2001 | Johnston et al. | |
| 6,190,556 B1 | 2/2001 | Uhlinger | |
| 6,197,193 B1 | 3/2001 | Archer | |
| 6,203,688 B1 | 3/2001 | Lipsztajn et al. | |
| 6,238,643 B1 | 5/2001 | Thangaraj et al. | |
| 6,274,041 B1 | 8/2001 | Williamson et al. | |
| 6,290,686 B1 | 9/2001 | Tanzer | |
| 6,312,598 B1 | 11/2001 | Munson et al. | |
| 6,355,093 B1 | 3/2002 | Schwartz et al. | |
| 6,368,510 B2 | 4/2002 | Friot | |
| 6,376,011 B1 | 4/2002 | Reeves et al. | |
| 6,395,678 B1 | 5/2002 | Summers et al. | |
| 6,428,696 B2 | 8/2002 | Kuke | |
| 6,432,322 B1 | 8/2002 | Speronello et al. | |
| 6,451,253 B1 | 9/2002 | Pitochelli et al. | |
| 6,458,162 B1 | 10/2002 | Kovlish et al. | |
| 6,458,735 B1 | 10/2002 | Klatte | |
| 6,461,514 B1 | 10/2002 | Al-Samadi | |
| 6,464,672 B1 | 10/2002 | Buckley | |
| 6,468,942 B1 | 10/2002 | Sansalone | |
| 6,503,419 B2 * | 1/2003 | Klatte | 252/187.23 |
| 6,552,141 B1 | 4/2003 | Chmelir et al. | |
| 6,575,961 B2 | 6/2003 | Joshi | |
| 6,605,304 B1 | 8/2003 | Wellinghoff et al. | |
| 6,607,668 B2 | 8/2003 | Rela | |
| 6,677,256 B1 | 1/2004 | Sun et al. | |
| 6,712,974 B1 | 3/2004 | Palm et al. | |
| 6,764,661 B1 * | 7/2004 | Girard | 422/305 |
| 6,790,427 B2 * | 9/2004 | Charles et al. | 423/478 |
| 6,821,435 B1 | 11/2004 | Lindquist et al. | |
| 6,833,075 B2 | 12/2004 | Hughes | |
| 6,861,002 B2 | 3/2005 | Hughes | |
| 6,878,285 B2 | 4/2005 | Hughes | |
| 6,957,743 B2 | 10/2005 | Johnston et al. | |
| 7,172,646 B2 * | 2/2007 | Tempel et al. | 95/241 |
| 2002/0006427 A1 | 1/2002 | Umezu et al. | |
| 2002/0158007 A1 | 10/2002 | Li | |
| 2003/0015467 A1 | 1/2003 | Johnston et al. | |
| 2003/0118503 A1 * | 6/2003 | Pu et al. | 423/478 |
| 2003/0173287 A1 | 9/2003 | Johnston et al. | |
| 2003/0196955 A1 | 10/2003 | Hughes | |
| 2003/0196959 A1 | 10/2003 | Hughes | |
| 2003/0196960 A1 | 10/2003 | Hughes | |
| 2003/0196966 A1 | 10/2003 | Hughes | |
| 2004/0149634 A1 | 8/2004 | Hughes | |
| 2004/0159605 A1 | 8/2004 | Hughes | |
| 2004/0232068 A1 | 11/2004 | Johnston et al. | |
| 2005/0098495 A1 | 5/2005 | Hughes | |

| | | | | | |
|---|---|---|---|---|---|
| 2006/0060818 A1 * | 3/2006 | Tempel et al. ........... 252/181.3 | JP | 2000-211901 A * | 8/2000 |
| | | | WO | WO 99/26987 | 6/1999 |
| | FOREIGN PATENT DOCUMENTS | | WO | WO 02/30766 | 4/2002 |
| | | | WO | WO 2004/071960 A2 | 8/2004 |
| JP | 59145087 A | 8/1984 | | | |
| JP | 62204892 | 9/1987 | * cited by examiner | | |

MATERIALS FOR STORING AND RELEASING REACTIVE GASES

CROSS-REFERENCE TO RELATED APPLICATIONS

This application claims the benefit of U.S. Provisional Application No. 60/557,146, filed Mar. 26, 2004. The application is incorporated herein by reference in its entirety.

BACKGROUND OF THE INVENTION

The field of this invention is generally related to the generation and containment of solutions incorporating reactive gases and their precursors.

Reactive and inert gases have significant utility in modern society. Therefore, significant effort has been expended in the development of methods to isolate, concentrate, store, and transport highly purified single compositions as well as mixtures of gases with specific component ratios. The beneficial characteristics of gases such as chlorine dioxide, oxygen, sulfur dioxide, carbon dioxide, chlorine, and nitrogen containing gases are known in many fields. These gases modify solution properties by interacting with both chemical and biological components contained therein.

Methods have been extensively described for generating and packaging many reactive gases for transportation and for storage on-site when continual use is required. However, a particular distinction must be made concerning chlorine dioxide gas generation, storage, and transport, because chlorine dioxide is a highly reactive gas, which cannot be compressed, contained/stored, or transported like many other gases. Chlorine dioxide thus must be generated as needed at the site of application. While this gas has exceptional utility, the inability to store it has limited its widespread use. For instance, this gas has been difficult to utilize in many small volume, low concentration applications, and by consumers in residential applications.

Safe, convenient, batch mode preparation of small volumes of chlorine dioxide gas, sulfur dioxide, carbon dioxide, chlorine, gases which contain nitrogen, and other reactive gases continues to receive the attention and interest of many research and development groups. While carbon dioxide and sulfur dioxide, as well as nitrogen-containing gases, are easily stored and transported, the requirements for storage and transport of chlorine dioxide precursor reagents, as well as generation of the gas, are much more complicated. Chlorine dioxide is commonly generated in batch mode through the mixing of metal chlorite and acidic solutions or solutions containing chlorine-based oxidizers.

The patent literature and prior art associated with the storage of chlorine dioxide precursor reagents, and the generation of chlorine dioxide gas can be generally classified into three arenas. The first arena is directed toward mechanical devices and their methods of use. These mechanical devices target the controlled mixing and reaction of chlorine dioxide precursor reagents, separation of the product gas from the reaction solution, increasing the efficiency of reagent use, and ultimately controlling the delivery of gas into a liquid or gas phase system. Examples in this arena are disclosed in U.S. Pat. Nos. 4,683,039, 6,428,696, 6,203,688, and 5,415,759.

The second arena is directed toward powdered materials which contain all or some of the chlorine dioxide precursor reagents and their methods of use. These chemical systems target the protective storage of the precursor reagents, the mechanism of exposure of the dry powder and precursor reagents to water, and the interaction of the powdered components and precursor reagents with activators, to generate chlorine dioxide. Important considerations in the design of these powdered systems include the concentration of precursor reagents, the stability of the precursor reagents, the need for activating agents, sensitivity to liquid and vapor water, and the rate and duration at which chlorine dioxide gas can be generated. In the majority of powdered and compressed powder systems silicates, zeolites, and desiccants are used to carry the precursor reagents for generating chlorine dioxide and for protecting the reagents from water. Many preparations require spray drying or other rapid means of removing water from the precursor reagents. Exposure to water often initiates reactions yielding chlorine dioxide gas. Much of this prior art requires sophisticated control of materials, chemical reagents, and powder processing technical know-how and specialized packaging. These requirements limit the range of gas concentrations that can be generated, the rate and duration of gas release, and ultimately the types of applications that can be addressed with these materials. Examples in this arena are disclosed in U.S. Pat. Nos. 6,238,643, 6,432,322, 6,605,304, 4,585,482, 6,503,419, and 6,458,735.

The third arena involves the use of solutions which contain the precursor reagents for chlorine dioxide generation. These solutions are often referred to as stabilized chlorine dioxide and usually consist of an aqueous solution of sodium chlorite with an alkaline pH. Exposure of these solutions to an activator, a powdered or aqueous acid solution, yields chlorine dioxide gas. Packets of liquid and powdered reagents are usually combined in a large volume vessel and then diluted with water for application.

Manipulation of concentrated solutions containing both precursor reagents and the reactive gas require extreme care and thus many products utilize dilute solutions of reagents. Additionally, viscous solutions of stabilized chlorine dioxide precursor reagents and/or chlorine dioxide gas containing solutions have been disclosed. These viscous solutions are prepared through the addition of polymer additives commonly used in the food and cosmetic industries. These highly viscous materials, while suitable for niche applications such as skin lotions, are inconvenient and difficult to use in many atmospheric, liquid and solid surface treatment applications. Examples in this arena are disclosed in U.S. Pat. Nos. 4,084,747, 4,330,531, and 6,451,253.

Accordingly, there remains a need for new materials and methods for generating reactive gases, materials and methods which facilitate the storage and transport of gas precursor reagents, materials and methods which facilitate the preparation of solutions which contain a wide range of reactive gas concentrations, and materials and methods which can serve as a platform for safe, inexpensive, and consumer friendly products.

SUMMARY OF THE INVENTION

Compositions, methods, and devices are provided for use in containing and releasing a gas, particularly a reactive gas. In one aspect, a composition is provided that includes a reactive gas, reactive gas precursor, or combination thereof; a fluid in which the reactive gas, reactive gas precursor, or combination thereof is dissolved; and a solid material in which fluid is absorbed or adsorbed, wherein the solid material controls the formation or release of the reactive gas. Examples of reactive gases include chlorine, bromine, iodine, carbon dioxide, oxygen, nitrogen, sulfur dioxide, hydrogen sulfide, hydrogen cyanide, chlorine monoxide, nitrogen monoxide, and nitrogen dioxide. A preferred reactive gas is chlorine dioxide.

In various embodiments, the reactive gas precursor comprises a cation, an acid, an oxidation agent, a reduction agent, a base, an anion, or a combination thereof. For example, the reactive gas precursor can comprises an organic acid, an inorganic acid, or a combination thereof. Examples of suitable organic acids include carboxylic acids, esters, anhydrides, acyl halides, amines, and polymers. Examples of suitable inorganic acids include hydrofluoric acid, hydrochloric acid, hydrosulfuric acid, hydrobromic acid, hydroiodic acid, phosphoric acid, boric acid, silic phosphate esters, trialkylsilylphosphate, sulfonic acid esters, sulfonic acid chlorides, phosphosilicates, phosphosilicate anhydrides, phosphosiloxanes, tetraalkyl ammonium phosphates, monobasic phosphates, polymetaphosphates, borophosphates, aluminophosphates, silicophosphates, polyphosphates, and metal salts. In one embodiment, the reactive gas precursor comprises an anion selected from chlorite, chlorate, sulfite, bisulfite, sulfide, sulfate, carbonate, bicarbonate, cyanide, hypochlorite, nitrite, nitrate, hydroxide, chloride, bromide, iodide, and fluoride. In another embodiment, the reactive gas precursor comprises an oxidizing agent selected from hypochlorite, hypochlorous acid, ozone, peroxide, and monopersulfate. A preferred reactive gas precursor comprises a chlorite salt or chlorate salt.

In one embodiment, the fluid comprises a polar liquid, such as water, an aqueous solution, an alcohol, or an amine. In another embodiment, the fluid comprises a non-polar liquid.

In preferred embodiments, the solid material is in the form of particles, woven fibers, nonwoven fibers, sponges, sheets, films, foams, or a combination thereof. In one embodiment, the solid material comprises a polymer. In certain embodiments, the polymer comprises an acid polymer selected from polylactic acids, polyglycolic acids, polyacrylic acids, polyacrylamides, polyesters, polyhydroxis, polyalcohols, polyanhydrides, and gums. In one embodiment, the polymer comprises a polycarbonate. In another embodiment, the solid material comprises a mineral, e.g., in particulate form.

In one embodiment, the composition further includes a second solid material that does not appreciably absorb the liquid solution. This second material can, for example, be in the form of particles, fibers, sheets, films, or combinations thereof.

The composition can be modified by various means. In one embodiment, the solid material further includes at least one surface modifying agent. In another embodiment, the fluid further includes one or more dissolved agents. Examples of the dissolved agents include electrolytes, fragrances, sweeteners, coloring agents, chelating agents, ligands, nutritional substances, viscosity modifiers, metal ions, pH modifiers, buffers, solubility modifiers, precipitation agents, flocculation agents, surfactants, fluorine containing polymers, emulsions, enzymes, nucleic acids, and proteins.

In a preferred embodiment, a composition is provided for use in containing and releasing chlorine dioxide gas comprising a liquid solution of a chlorate salt, a chlorite salt, chlorine dioxide, or a combination thereof; and polymeric particles or fibers, in which the liquid solution is absorbed, wherein the polymeric particles or fibers control the release of chlorine dioxide. For instance, the polymeric particles or fibers can comprise an acid polymer.

In another aspect, a device is provided which comprises a container having an enclosed cavity in which the compositions described above are disposed. In one embodiment, the container comprises a gas permeable wall through which a reactive gas released from the composition can diffuse out of the device. The device can be tailored to release a range of different reactive gases, including, for example, chlorine dioxide, chlorine, bromine, iodine, carbon dioxide, oxygen, nitrogen, sulfur dioxide, hydrogen sulfide, hydrogen cyanide, chlorine monoxide, nitrogen monoxide, and nitrogen dioxide. In a preferred embodiment, the composition comprises particles or fibers of a polymeric material or inorganic material. In one embodiment, the container comprises a sachet comprised of a polymeric sheet or film. In one embodiment, the device further includes at least a pair of electrodes connected to a power source, the electrodes being positioned to pass an electric current or voltage through the composition, effective for example to electrochemically generate the reactive gas.

In another aspect, a method is provided for making a composition for the containment and release of a reactive gas. In one embodiment, the solid material is in the form of particles or fibers. In a preferred embodiment, the methods comprises: dissolving a first reactive gas precursor in a fluid to form a solution; absorbing or adsorbing the solution in an absorbent solid material; and exposing the solid material to a second reactive gas to generate a reactive gas in the solid material, which is substantially non-reactive with the reactive gas, the fluid, or the reactive gas precursors. In another embodiment, the second reactive gas precursor is in the form of an acidic, oxidizing, or reducing gas. In still another embodiment, the second reactive gas precursor is in powder form or in the form of an aqueous solution. In yet another embodiment, the second reactive gas precursor is in a solution absorbed in a second solid material. In a preferred method the first and second reactive gas precursors are selected to produce a reactive gas, such as chlorine dioxide, chlorine, bromine, iodine, carbon dioxide, oxygen, nitrogen, sulfur dioxide, hydrogen sulfide, hydrogen cyanide, chlorine monoxide, nitrogen monoxide, and nitrogen dioxide.

DETAILED DESCRIPTION OF THE INVENTION

Figure 1:
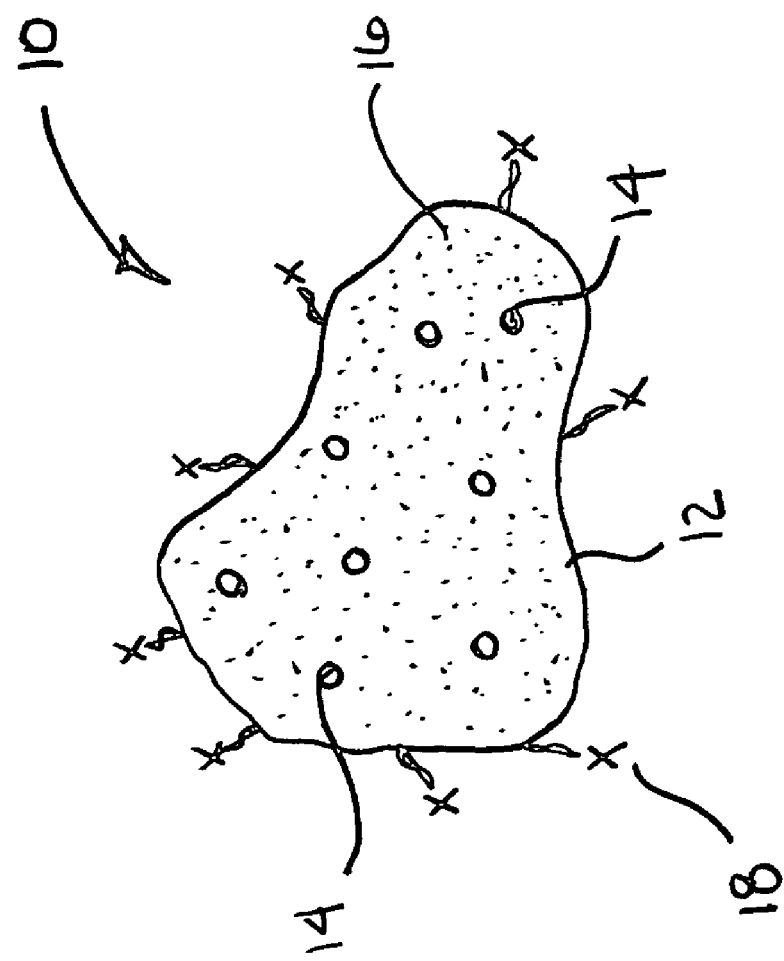
FIG. 1 is an illustration of one embodiment of the compositions described herein, showing a polymer particle with surface reactive groups which contains an aqueous solution of chlorite metal salt and chlorine dioxide.

Compositions, formulations, devices, and methods have been developed for safely and efficiently generating, containing, and utilizing gases in a wide range of concentrations. The materials and methods provided herein, while widely applicable to many different gases, are ideally suited for the manipulation of reactive gases, and more specifically, to reactive gases that have unique generation, storage, and delivery characteristics. An exemplary gas is chlorine dioxide. The materials and methods allow rapid and safe generation, transfer, and application of high concentrations of chlorine dioxide gas in solid, liquid, and gas phase systems and are suitable for all known uses of chlorine dioxide. Examples of other reactive gases that can be generated and used as described herein include sulfur dioxide, carbon dioxide, chlorine, oxygen, and gases which contain nitrogen.

These materials, formulations, and devices can be applied widely as disinfectants, odor control agents, decontamination and fumigation agents, liquid, gas, and air treatment materials, respiratory agents, food and beverage processing agents, neutralization agents, and in many industrial, residential, medical and military surface treatment operations. The materials and methods described herein can facilitate the fabrication and wide dissemination of many new consumer, medical, industrial, and military useful materials and products.

As used herein, the terms "comprise," "comprising," "include," and "including" are intended to be open, non-limiting terms, unless the contrary is expressly indicated.

Overview of the Reactive Solution Materials and Methods

In preferred embodiments, methods, compositions, and articles are provided for the generation of a reactive gas in association with particles or fibers that have the capacity to retain and control liquids. The particles, fibers, or combinations thereof, contain and control the gas precursor reagents and generated gases, and transfer or deliver a liquid-gas composition in a solid-like form. Particles and fibers containing liquids and dissolved gases may be used directly in applications through direct contact or indirectly through transfer of the particle or fibers contents to a secondary solution. These liquid and gas containing particles and fibers may be further mixed with adsorbent particles or fibers to provide unique solid, liquid, and gas treatment materials. This unique combination of solids, liquids, and gases facilitates many new consumer, industrial, medical, and military product designs.

The materials and methods involve the use of adsorbent and absorbent materials for storing and transporting the precursor reagents, generating the reactive gases, using liquids as reactive gas storage depots, and facilitating the delivery of the gas with additional chemical agents which are associated with use of the reactive gases. The materials and methods do not require the use of silicate, zeolite, desiccant, or common tablet preparation compounds to produce materials that are convenient to handle and apply, and to store the sensitive precursor reagents. The materials and methods do not require sophisticated drying or packaging technologies.

Reactive gases are used in the treatment of gaseous environments, liquids for ingestion, solutions for cleaning, and for treatment of surfaces, instruments, and solid materials. While many reactive gases can be safely generated, stored, and transported, some reactive gases have chemical characteristics that preclude these practical activities. As a result, such gases must be generated at the site of application through chemical reactions with precursor reagents and used immediately. The present methods and compositions provide simple and rapid preparation of small volumes of reactive gases allows chemical reagents to be used efficiently and cost effectively, and to reduce deleterious effects on the environment.

In a preferred embodiment, the reactive gas is chlorine dioxide. Chlorine dioxide has numerous beneficial characteristics making it unique for treating gas phase systems such as breathing air, ventilation systems, for odor control, for treating liquid phase and solid phase systems. Chlorine dioxide is highly water-soluble and does not dissociate into ions. Sub-part-per-million (ppm) aqueous concentrations are useful in treating drinking water for chemical and biological contaminants, while higher concentrations (>50 ppm) are useful for disinfecting and sanitizing liquids, solid surfaces, and porous materials. At even higher concentrations, the gas can be used to sterilize materials and equipment useful in the medical and surgical fields. The biocidal, chemical reactivity, and odor neutralizing characteristics of chlorine dioxide are well known in the fields of food processing, water treatment, wound treatment, paper and textile, and military decontamination. The present methods and compositions will more practically enable these and additional chlorine dioxide applications. In some other embodiments, the methods and compositions are used in the generation and storage of carbon dioxide, sulfur dioxide, chlorine-containing gases, and nitrogen-containing gases.

Examples of other reactive gases applicable to the present methods and materials include carbon dioxide, sulfur dioxide, hydrogen sulfide, ammonia, chlorine gas, dichlorine monoxide, hydrocyanic acid, nitrogen dioxide, nitrogen oxide, hydrogen, nitrogen, and oxygen.

The present methods and compositions involve the manipulation of reactive gas precursor reagents and reactive gases through the use of liquids and liquid absorbent and adsorbent materials. In preferred embodiments, all components are stable in high concentrations of the gas precursor reagents, solution stabilizers, activating agents, and the generated reactive gases. Proper selection of the liquid component facilitates high capacity storage of the reactive gas once generated. The capacity for storing gases is directly related to the solubility of the gas in the liquid, which is governed by temperature and pressure, as well as the chemical composition of the liquid or solution.

Many possible combinations of gas precursor reagents, liquids with gas solubility (storage capacity), and absorbent articles are provided for control and manipulation of all components. In general, the methods and compositions involve the combination of absorbent/adsorbent materials that have limited reaction with the precursor reagents, reactive gas precursor reagents, and a liquid in which the gas precursor reagents, the generated gas, or a combination thereof have solubility.

In various embodiments, the absorbent and adsorbent materials include natural and synthetic polymers in particle, fiber, or sheet form; natural and synthetic materials such as sponges; or natural and synthetic minerals that have substantial liquid carrying capacity. Many of these materials can swell or expand upon liquid uptake and provide strong liquid retention even under pressure. The absorbent materials are utilized in a manner which allows rapid mixing and reaction of gas precursor reagents, controlled distribution and delivery of gases, and a reservoir or depot for both reagents and gases. This depot of reagents and reactive gases in solid form provides safety and convenience in utility and ultimately in application of high concentrations of the reactive gases.

By utilizing absorbent/adsorbent materials (e.g., particles, fibers, a combination thereof) in combination with dissolved gas precursor reagents, the gas generating reactions can be controlled, and liquids with high concentrations of the reactive gas can be safely manipulated and stored. Preferred absorbent and adsorbent materials are stable in highly caustic and acidic solutions and can retain these hazardous solutions for long periods. By containing the solutions and gases, hazards associated with handling these chemicals are significantly reduced. In one embodiment, the particles and fibers are selected to permit the liquids to be handled as powders and through proper particle and fiber size control allow the precise delivery of known concentrations of gas precursor reagents and reactive gases.

The absorbent/adsorbent materials can be combined with the liquids and the reactive gas precursor agents via several simple methods. In general, particles and fibers can be prepared with the individual precursor reagents of the gas generation reaction. Specifically, different particles and fibers are used to contain a single gas precursor reagent. When separate particle types are mixed, the precursor reagents contained react through bulk fluid transfer and diffusion, ultimately yielding particles with similar composition, and containing the generated gas to the capacity of the liquid. Gas in excess of the solubility limit, as determined by chemical and physical parameters of the liquid, will escape to the surrounding solution or atmosphere.

Alternatively, all components; particles, fibers, or combinations thereof; and precursor reagents may be combined into a single composite in dry form. Upon exposure to a liquid, the gas precursor reagents react, gas is generated, and the liquids and gases are contained by the particles, fibers, or combinations thereof. Further alternative methods include introducing one of the precursor reagents in dry form or gaseous form to the components, particles, fibers, or combinations thereof, which contain a solution of the precursor reagents. Upon exposure to the liquid containing particles or fibers, the dry or gaseous reagents dissolve and react, again yielding gas and liquids which are absorbed/adsorbed by the particles and/or fibers.

Alternatively, the particles and fibers that carry dissolved precursor reagents may be directly reacted in electrochemical systems. In these systems, electrodes and a power source are used to generate the gas. The gas is dissolved in the liquids which are contained by the particles or fibers. Furthermore, the particles can obtain precursor reagents through direct chemical or electrochemical reaction before gas generation reactions are initiated. For example, acidic liquids can be generated in the particles and fibers through electrochemical reaction of compounds, such as water, that are contained in the particles or fibers. Similarly, chloride ions can be electrochemically oxidized to free chlorine, which reacts quickly when chlorite is present or introduced into solution.

Many of the preferred synthetic polymers and minerals are those that are stable in concentrated acids and bases, and that strongly absorb and retain solutions of these chemicals. Such materials do not release the absorbed liquid easily by applying external pressure. The liquids contained in these materials serve as both a storage depot for the molecules and ions that react to form the reactive gases, as well as the generated gas.

In some embodiments, the particles or fibers contain additional chemicals that are useful in combination with the generated gas and precursor reagents. Representative examples include pH modifiers, ion controlling agents, colored indicators, fragrances, and surfactants. In other embodiments, the particles or fibers are mixed with non-liquid containing particles and fibers for preparation of unique treatment materials. In still other embodiments, the particles or fibers are combined with and contained in membrane materials or materials having selective and defined porosity for controlling the kinetics of release of the reactive gas to the surroundings, to control exposure of the particles or fibers to one or more components in the surrounding atmosphere or other environment.

In one aspect, a method is provided to conveniently and safely mix hazardous solutions that contain chlorine, sulfur, carbon, oxygen, and nitrogen compounds, caustics, acids, and a wide range of chemical reagents that yield gases and useful chemical agents. In another aspect, a convenient method is provided for storing reactive gases and subsequently delivering the reactive gases to a site of application. Typically, the materials and methods provided are environmentally benign in that they can readily utilize natural and synthetic materials which are biodegradable. In addition, absorbent materials exist for hydrophobic and non-polar liquids and these materials in combinations with their associated liquids are capable of acting as storage depots for chemical reagents and the reaction products of those chemical reactions, including gases. It is possible to extract gases between particle types and solvent types. The materials and methods provided herein have significant utility and benefits not available with known, convention means for reactive gas generation, manipulation, and application.

Additional Details of the Materials and Methods

Chemical and Physical Properties

Chlorine dioxide is very soluble in water and aqueous solutions and has been determined to be stable in concentrations of approximately 10 g/L. Solubility is a function of temperature, pressure, and chemical composition of the liquid. Unlike carbon dioxide or chlorine gas, chlorine dioxide does not ionize in solution, and remains a true gas. Concentrated solutions of chlorine dioxide are pale yellow to brown in color and have an odor similar to chlorine. Gases such as chlorine, carbon dioxide, sulfur dioxide, and nitrogen containing gases also have significant solubility in solvents such as water.

Although chlorine dioxide contains chlorine, its reaction chemistry is predominantly through oxidation and not chlorination. This characteristic is highly beneficial as chlorinated reaction byproducts are undesirable in many applications including drinking water treatment. Additionally, chlorine dioxide is an efficient and rapid oxidizer of dissolved iron and manganese.

Chlorine dioxide is very reactive towards phenols and sulfur containing molecules and thus is an efficacious odor control agent and decolorizing agent. Unlike the hypochlorite-hypochlorous acid system, chlorine dioxide is very effective over a broad solution pH range.

Generation of Chlorine Dioxide

Chlorine dioxide can be generated from both solid and solution phase reactions. Reactions for preparing batches of chlorine dioxide include acidifying solutions of metal chlorite, introduction of a strong oxidizing agent such as hypochlorite into solutions of chlorite, or direct electrochemical oxidation of chlorite. Metal chlorate solutions may also be utilized in combination with chemical and electrochemical reduction reactions.

A variety of methods can be used to prepare the materials. The reactive gas chlorine dioxide is used to exemplify the materials, methods and utility. For instance, chlorine dioxide can be generated with solution phase, solid phase, and gas phase reactions in particles, composed of polymers and containing aqueous solutions. In another embodiment, chlorine dioxide gas is generated by known external means and then is loaded into aqueous solution containing polymer particles through direct exposure. In yet another embodiment, the chlorine dioxide gas is generated in particles by exposing particles containing chlorite to an electrode surface. Chlorine dioxide is transferred to a secondary solution by transfer of polymer particles containing the gas.

Methods of Producing the Compositions and Materials

In a preferred embodiment, absorbent and adsorbent materials are combined with reactive gas precursor reagents, and a liquid in which one or all gas related components exhibit solubility. The materials also may contain soluble and/or suspended chemical and biological components in addition to the gas precursor reagents and the resultant gases. Additionally, the materials may simultaneously carry multiple gas species.

In one embodiment, the reactive gases are prepared from simple or complex salts. In preparing the materials, the gas precursor reagents can be utilized in dry powder form, dissolved in a solvent, or when applicable, in a gaseous state. The liquids incorporated into the materials may be present prior to or during, or after gas generation. Gases also may be directly loaded into particles and fibers containing solutions through exposure to the gas, which is generated by external means. Detailed descriptions of suitable gas precursor reagents and methods for preparing examples of the reactive gases of the invention are provided herein.

Chlorine Dioxide

Chlorine dioxide can be generated from solutions that contain the anion chlorite and an associated counter ion. Suitable chlorite sources include alkali metal chlorites, such as sodium, lithium, and potassium chlorites, alkaline earth chlorites such as calcium and magnesium chlorite, chlorite salts of transition metals, chlorite salts of primary, secondary, and tertiary amines including ammonium chlorite, trialkylammonium chlorite and quaternary ammonium chlorite. Those skilled in the art will recognize that other chlorite salts are possible and the final application of the material will determine the optimum precursor species. Exemplary chlorite salts are those based on alkali metals.

Chlorine dioxide may also be generated using chlorate anions and an associated counter ion. Suitable chlorate sources include alkali metal chlorates, such as sodium, lithium, and potassium chlorates, alkaline earth chlorates such as calcium and magnesium chlorate, chlorate salts of transition metals, chlorate salts of primary, secondary, and tertiary amines including ammonium chlorate, trialkylammonium chlorate and quaternary ammonium chlorate. Those skilled in the art will recognize that other chlorate salts are possible and the final application of the material will determine the optimum precursor species. Exemplary chlorate salts include those based on alkali metals.

Carbon Dioxide

Carbon dioxide gas can be generated from solutions that contain the anions carbonate and bicarbonate and an associated counter ion. Suitable salts of these anions include alkali metal bicarbonates including sodium bicarbonate, potassium bicarbonate, and lithium bicarbonate, alkaline earth metal bicarbonates and carbonates, including calcium bicarbonate and calcium carbonate and magnesium bicarbonate and magnesium carbonate, bicarbonates and carbonates of primary secondary, tertiary and quaternary amines such as ammonium bicarbonate. A wide range of transition metal bicarbonates and carbonates may be used. Those skilled in the art will recognize that carbonate and bicarbonate are anions whose concentrations are also controlled in solution by adjustment of solution pH. The skilled artisan will also recognize that many cationic polymer functionalities can provide the anions. Exemplary anions for generating carbon dioxide include the alkali metal bicarbonates.

Sulfur-Containing Gases

Sulfur containing gases, such as sulfur dioxide and hydrogen sulfide can be generated from solutions that contain the anions sulfite, bisulfite and sulfide and an associated counter ion. Suitable sulfite and bisulfite salts include alkali metals salts of bisulfite and sulfite including sodium, potassium, and lithium, alkali earth metal bisulfites and sulfites, such as calcium and magnesium bisulfite and sulfite, and transition metal bisulfites and sulfites. Charged primary, secondary, tertiary, and quaternary amines of sulfites and bisulfites can be used. Suitable sulfide salts include alkali metals salts of sulfide including sodium, potassium, and lithium, alkali earth metal sulfides such as calcium and magnesium sulfides, and transition metal sulfides. Charged primary, secondary, tertiary, and quaternary amines of sulfides can be used. Those skilled in the art will also recognize that many cationic polymers can provide the anions. Those skilled in the art will recognize that sulfite, bisulfite, and sulfide are anions whose concentrations are also controlled in solution by adjustment of solution pH. Those skilled in the art will also recognize that many cationic polymer functionalities can provide the anions. Exemplary salts for generating sulfur containing gases such as sulfur dioxide and hydrogen sulfide include the alkali metal sulfites, bisulfites, and sulfides.

Nitrogen-Containing Gases

Nitrogen containing gases, including nitrogen, nitrogen dioxide, and nitrogen oxide, can be generated from solutions that contain the anions nitrate and nitrite and an associated counter ion. Suitable salts of these anions include alkali metal nitrites and nitrates including sodium, potassium, lithium nitrite and nitrate, alkaline earth metal nitrites and nitrates, including calcium nitrite and nitrate and magnesium nitrite and nitrate and nitrites and nitrates of primary secondary, tertiary and quaternary amines such as ammonium nitrite and ammonium nitrate. A wide range of transition metal nitrites and nitrates may be used. Those skilled in the art will recognize that nitrite and nitrate are anions whose concentrations are also controlled in solution by adjustment of oxidation reduction potentials. Those skilled in the art will also recognize that many cationic polymer functionalities can provide the anions. Exemplary salts for generating nitrogen gases include the alkali metal nitrites.

Chlorine-Containing Gases

Chlorine containing gases, including chlorine and chlorine monoxide, can be generated from solutions that contain the anion hypochlorite and an associated counter ion. Suitable salts of this anion include alkali metal hypochlorites including sodium, potassium, and lithium hypochlorite, alkaline earth metal hypochlorites, including calcium and magnesium hypochlorite and hypochlorites of primary secondary, tertiary and quaternary amines. A wide range of transition metal bicarbonates and carbonates may be used. Those skilled in the art will recognize that hypochlorite anion concentrations are also controlled in solution by adjustment of solution pH. Those skilled in the art also will recognize that many cationic polymer functionalities can provide the anions. Stabilized hypochlorite/hypochlorous acid solutions may also be used. Exemplary salts for generating chlorine containing gases include the alkali metal hypochlorites.

Cyanide Gas

Cyanide gas can be generated from solutions that contain the cyanide anion and a counter ion. Suitable salts of this anion include alkali metal cyanides including sodium, potassium, and lithium cyanide, alkaline earth metal cyanides, including calcium and magnesium cyanide and cyanides of primary secondary, tertiary and quaternary amines. A wide range of transition metal cyanides may be used. Those skilled in the art will recognize that cyanide anion concentrations are also controlled in solution by adjustment of solution pH. Those skilled in the art will also recognize that many cationic polymer functionalities can provide the anions. Exemplary salts for generating cyanide gases include the alkali metal cyanides.

Oxygen Gas

Oxygen gas can be generated from solutions that contain peroxides or compounds generating peroxides, including organic or inorganic peroxides, peracids, or persalts. Preferred agents include hydrogen peroxide, peracetic acid, and monoperoxysulfate. A number of peroxides, peracids, and persalts are described in U.S. Pat. No. 4,964,870 to Fong, which is incorporated herein by reference.

Acids Used to Generate Gases

Many of the exemplary reactive gases can be generated by exposure of the gas precursor anions to acidic liquids, gases, or a combination thereof. Acids, and more particular hydronium ions or protons, can be provided by a wide range of chemical agents and through the presence of degradable chemical agents. Acid generating agents include water, protonated solvents such as alcohols, organic acids and inorganic acids. Acid provided by organic agents includes carboxylic acids; examples include acetic acids and naturally occurring acids. Both tartaric and citric acids are excellent agents for generating the reactive gases. Acid provided by organic agents also include esters, anhydrides, acyl halides, carboxylates of polyhydroxyalcohols, degradable polyesters including polylactic acid, polyglycolic acid, polyacrylic acid and copolymers, polyacrylamide and copolymers, poly-beta-hydroxybutyrate, polylactone, anhydride or phosphate esters blended with or grafted to polypropylene, polyethylene, or polystyrene.

Acid anhydrides include organic acid anhydrides, mixed organic anhydrides, homopolymers of organic acid anhydrides, mixed inorganic acid anhydrides, copolymers of organic acid anhydrides, and mixed organic acid anhydrides containing conjugation. Exemplary anhydrides include polymers containing anhydrides, including maleic anhydride, methacrylic anhydride, acetic anhydride, propionic anhydride, succininc anhydride, vinyl, styrene, or alkene containing polymers, as well as polymers including esters of lactic and glycolic acid monomers.

Many polymers, copolymers, and grafted polymers are capable of providing hydronium ions and protons for gas generation. Exemplary polymers include xanthum gum, polyvinylpyrrooidone, polyvinylalcohols, polyanhydrides, polyacrylamides, lactic acid based polymers, glycolic polymers, hydroxyl acids, and mixtures thereof. Those experienced in the art will recognize that the amount of polymer-sourced acid provided to a system is based upon polymer molecular weight, amount of polymer present, and solubility characteristics of the different chemical species.

Inorganic chemical species and chemical agents that contain halides, phosphorus, silicon, sulfur and boron are excellent sources of acid for generating the reactive gases. Mineral acids, including hydrofluoric, hydrochloric, hydrosulfuric, hydrobromic, hydroiodic, phosphoric, boric, and silic acid are exemplary. The materials can use a wide concentration range of these acids including commercially available concentrates. Additional inorganic acid providing chemical species include phosphate esters, trialkylsilylphosphate, sulfonic acid esters, sulfonic acid chlorides, phosphosilicates, phosphosilicate anhydrides, phosphosiloxanes, tetraalkyl ammonium phosphates, monobasic phosphates based on alkali metals, polymetaphosphates based upon alkali metals, borophosphates, aluminophosphates, silicophosphates, polyphosphates such as sodium and potassium tripolyphosphate, and mixed tripolyphosphates. Particulate metals and metal oxides can provide acid in order to generate the reactive gases. Oxides based upon aluminum, iron, silicon, and transition metals are applicable. Suitable salts for generating acid include metal salts such as iron chloride, iron sulfate, zinc sulfate, zinc chloride, cobalt sulfate, cobalt chloride, manganese sulfate, manganese chloride, copper sulfate, copper chloride, and magnesium sulfate.

Bases Used to Inhibit Gas Formation

The reactive gas compositions and materials can include chemical agents to control, stabilize, or inhibit the generation of the reactive gases. For example, technical grade sodium chlorite is formulated with approximately twenty percent carbonate and sulfate species. The formulation yields a strongly alkaline pH upon dissolution. Alkaline pH solutions containing chlorite minimize the generation of chlorine dioxide gas. Bases and chemical species capable of reacting with acid compounds through neutralization of hydronium ions or accepting protons serve as a mechanism for inhibiting the reaction of acids with the anion precursors to the reactive gases. Exemplary chemical agents include caustics prepared with alkali metals including sodium, potassium, and lithium hydroxides, as well as alkaline earth hydroxides such as calcium and magnesium hydroxides. Amines such as ammonia and ammonium hydroxide have acid neutralization capacity, as do bicarbonates, carbonates, phosphates, sulfates, borates, and the salts of organic weak acids such as acetates. Those skilled in the art will recognize the wide range of available acid neutralization chemicals.

Reduction Agents Used to Inhibit Gas Formation

Chlorine dioxide gas can be generated through oxidation with chemical agents or through electrochemical reaction. Exemplary agents include chlorine based oxidizers. Suitable chlorine containing species include chlorine gas and hypochlorites based on alkali salts and alkali earth salts. Stabilized chlorine species using cyanuric acid are also useful oxidizing agents. Compounds that neutralize these chlorine based oxidizing agents inhibit the generation of chlorine dioxide gas. Exemplary neutralizing agents include bisulfites, thiosulfates, reduced metals, and activated carbons. Reducing agents also may be used to increase the temperature of the system, which allows further control over gas concentrations and delivery parameters. In some cases, portions of the oxidizing agent generated are used or sacrificed to increase system temperature.

Absorption and Absorption Materials

In preferred embodiments, the adsorptive or absorptive material is in the form of particles, fibers, or combinations thereof. In one embodiment, the particles have a size in the range of 0.05 µm through 100 mm. In one embodiment, the fibers have a diameter in the range of 0.05 µm through 100 mm. Particles and fibers that interact with solvents can have a widely varying particles size due to fluid uptake. Homogeneous and heterogeneous particle and fiber mixtures can be widely varying. Those skilled in the art will understand that particles and fiber size distributions affect many treatment parameters as well as safety.

The absorbent particles, fibers, or other material forms can be obtained from a variety of natural and synthetic sources. These particles and fibers can be entirely composed of organic materials, inorganic materials, or combinations thereof. Further, the absorbent materials may be homogeneous or heterogeneous in distribution of the different synthetic, natural, organic, or inorganic components. Those familiar with the technology and art of absorbency also understand that adsorption occurs at the surface of these materials and that both molecular scale and bulk scale solvent and solute interactions can occur in simultaneous and continuous fashion. In addition, those skilled in the art of preparing absorbent materials understand that nonwoven, woven, physically and chemical fiber treatment technologies as well as wrapping and layering sheets of materials, have considerable impact on material properties.

Suitable absorbent materials include sponges, foams, and absorbent minerals and polymers. These materials may be in the form of particles, fibers, sheets, or combinations thereof. Foams and sponge materials can hold and contain liquids in widely varying amounts based upon preparation methods. Sponge materials can be naturally occurring or synthetic. Applicable materials include polyethers, polyesters, polyurethanes, celluloses, polyethylenes, polyvinylalcohols, corks, and butyl rubbers and copolymers of the different species. Pore and cell type, open or closed, and size can be modified to change absorption properties. Foam materials can be further treated to be fire retardant, flexible, or semi-rigid. Manufacturing methods such as reticulation also affect absorbency. In addition, woven and nonwoven materials have the capacity to adsorb and absorb fluids. The type of fluids and capacity of uptake are dependent, for example, upon fiber types, manufacturing methods, and surface treatment. Foams, sponges, and fiber absorbents carry chemical compatibility characteristics related to their composition and method of manufacture. Those skilled in the art will understand the chemical compatibility requirements of the different materials.

Exemplary materials for holding liquid reagents include those materials such as super-absorbent polymers and absorbent minerals that do not release liquids upon changes in pressure and temperature. The capacity to tightly hold the liquids containing reactive precursor reagents required for reactive gas generation and subsequently liquids that contain high concentrations of reactive gases increase the safety in generating, storing, and applying reactive gases to a wide range of applications.

Preferably, the absorbent or adsorbent material is one that is stable in the presence of highly caustic solutions of metal chlorites, and chlorate solutions, in concentrated acids, and in the presence of high concentrations of reactive gases including chlorine dioxide, carbon dioxide, and gases containing nitrogen, oxygen, and sulfur. For instance, caustic solutions of sodium chlorite are known to be stable for long periods of time. Absorbent articles that are stable with both anions and caustic are suitable materials. Similarly, absorbent articles that are stable with both cations and acids are suitable materials. These materials each containing a different reactive species may be combined to yield the desired gas. After generation of the gas, the gas is soluble in the liquid contained by the materials. Materials that are stable to chlorine dioxide, carbon dioxide, and sulfur and nitrogen gases are well known.

Exemplary inorganic materials include smectic type minerals. Inorganic sources of liquid carrying and absorbent particles include aluminosilicates, smectic or montmorillinite clays, and preferred materials including bentonite, attipulgite, and expanded silica.

In a preferred embodiment, the absorbent material is generated from a range of synthetic and natural polymer materials. The class of materials known as "superabsorbents" is particularly suitable in this regard. Superabsorbents are natural, synthetic, or mixed polymers that are not fully cross-linked. They may be classified as polyelectrolyte or nonpolyelectrolyte types as well as covalent, ionic, or physical gelling materials. These materials have the capacity to absorb many times their own volume in fluid. Examples of synthetic materials include polyacrylic acids, polyacrylamides, poly-alcohols, polyamines, and polyethylene oxides.

Representative composite superabsorbent material include those selected from derivatives of polyacrylic acids, polyacrylamides, poly-alcohols, polyamines, polyethylene oxides, cellulose, chitins, gelatins, starch, polyvinyl alcohols and polyacrylic acid, polyacrylonitrile, carboxymethyl cellulose, alginic acids, carrageenans isolated from seaweeds, polysaccharides, pectins, xanthans, poly-(diallyldimethylammonium chloride), poly-vinylpyridine, poly-vinylbenzyltrimethyl ammonium salts, polyvinylacetates, polylactic acids, or combinations thereof. The composite material also may comprise a material selected from resins obtained by polymerizing derivatives of acrylic acid or resins obtained by polymerizing derivatives of acrylamide.

In one embodiment, the absorbent material comprises one or more biodegradable materials. Representative examples include cellulose derivatives, chitins, and gelatins. In addition, mixtures of synthetic polymer and natural polymers, either as distinct chains or in copolymers, can be used to generate these absorbent materials. Examples of such polymers include starch polyacrylic acid, polyvinyl alcohols and polyacrylic acid, starch and polyacrylonitrile, carboxymethyl cellulose, alginic acids carrageenans isolated from seaweeds, polysaccharides, pectins, xanthans, poly(diallyldimethylammonium chloride), polyvinylpyridine, polyvinylbenzyltrimethylammonium salts, cellulose, alginic acids, carrageenans isolated from seaweeds, polysaccharides, pectins, xanthans, starch, or combinations thereof, polyethyleneglycol, a polylactic acid, a polyvinylalcohol, a co-polylactideglycolide, cellulose, alginic acids, carrageenans isolated from seaweeds, polysaccharides, pectins, xanthans, and starch.

The process of cross-linking polymer chains derived from any source or combinations of sources is variable and will affect the magnitude of fluid absorption, and the types of fluids that can be absorbed. In addition, one skilled in the art will understand that molecular characteristics, such as polymer chain composition, functional group position, and distribution, as well as polymer molecular weight and distribution, will affect the performance of the material. The skilled artisan can modify these parameters to vary the properties of the resulting composite as needed to contain and release the reactive gas precursor, the fluid, or the reactive gas as desired. The volume capacity of a material is also subject to the type and composition of the fluid in which the material is exposed.

Addition of Soluble Salts and Other Soluble Compounds

The preferred materials provide control of liquids and gas-containing liquids and have the capacity to hold (adsorb/absorb) significant volumes of liquid (in some cases water or other polar solvents and other cases a nonpolar solvent). In addition to the gas precursor, reagents and gases, the absorbent material (e.g., particles or fibers) optionally can further include/contain soluble agents. Exemplary soluble agents include soluble metals, chelating agents, metal ligands, biocides, amines such as quaternary amines, organic acids such as fatty acid, micelles, and emulsions. Polar solvents such as alcohols, ethanolamines, and polar organic solvents with solubility in water are applicable and allow solubilization of active chemical and biological species. Many biological components including DNA, RNA, proteins, peptides, and associated molecules are soluble in water and polar solvents. Exemplary biological agents include, enzymes, protein fragments, and emulsions or micelles that contain these agents. Those skilled in the art will recognize that combinations of certain soluble, suspended, and reactive agents are not compatible and will neutralize or generate undesirable or unwanted chemical species. Additional exemplary agents include alcohols, fragrances, odor neutralizing agents, odor masking agents, disinfecting agents, preservatives, biocides, bacteriostats, fungistats, osmostic regulators, sequestering agents, chelating agents, and binders pesticides, insecticides, herbicides, pheromones, and animal attractants, cleaning solutions, fatty acids, soaps.

Addition of Solution Viscosity Modifiers

The absorbent/adsorbent material can contain, or be selected to contain, liquids with widely varying viscosities. In an optional embodiment, the liquid can be modified with one or more food-, medical-, or industrial-grade viscosity agents. Representative examples of such agents include magnesium containing minerals, betaines, celluloses, methylcelluloses, xanthum gums, acrylates, acrylamides, polyalcohols, polyethylenglycols, polyesters, and naturally occurring and synthetically produced polymers, copolymers, and grafted polymers. Those skilled in the art will understand the importance of molecular weight and solubility characteristics of these compounds when used as solution viscosity modifiers.

Addition of Suspended Particulate Material

In a further optional embodiment, the liquid of the reactive gas compositions includes suspended (i.e., insoluble) particulate or fibrid matter. Representative examples of such particles include microparticles or nanoparticles. The particles can be comprised of metals, alloys, metal oxides, or combinations thereof. Nanoparticles optionally can include surface reactive chemicals such as metal ions and organic functionalities. Preferred and applicable materials include naturally occurring, synthetic, and recycled materials. Suitable materials include insoluble phosphate containing minerals selected from calcium phosphates, iron phosphates, manganese phosphates, aluminum phosphates, magnesium phosphates, silver phosphates, copper phosphates, zinc phosphates, zirconium phosphates, calcium monophosphates, diphosphates, tricalcium phosphates, octaphosphate, metaphosphates, metal oxides selected such as aluminum oxides, iron oxides, magnesium oxides, calcium oxides, manganese oxides, zinc oxides, copper oxides, titanium oxides, silicon oxides, aluminum containing minerals such as alumina bauxite, kaoline, iron containing minerals such as iron oxide, amorphous hydrous ferric oxide, maghemite, hematite, goethite, lepidocrocite, manganese containing minerals such as manganese oxide, pyrolusite, silica containing minerals including silica, quartz, metals such as iron, copper, manganese, silver, gold, platinum, rhodium, zinc, alloys prepared from iron, copper, zinc, carbon, chromium, manganese, nickel, carbonates such as calcium carbonate, magnesium carbonate, iron carbonate, aluminum carbonate, sulfates including magnesium sulfate and calcium sulfate, hydroxides such as aluminum hydroxide, iron hydroxide, magnesium hydroxide, calcium hydroxide, and copper hydroxide. Synthetic and natural fibers, including strings, yarns and textiles including, cotton, wool, polypropylene, rayon, polyester, nylon, acrylic are also applicable.

Addition of Non-Solvent Carrying Particles

Optionally, the materials (e.g., particles, fibers) that have the capacity to uptake and contain liquids and gas precursor reagents can be mixed and combined, in simple or complex methods, with other solid materials (such as particles, fibers, or a combination thereof) that have little or no fluid uptake or solution control capability. In one embodiment, these non-absorbing particles or fibers have a size (e.g., diameter) in the range of 0.05 μm through 100 mm. These materials may obtain surface bound solvent; they are usually prepared for use by drying techniques. Exemplary materials include desiccants, amorphous silicates, zeolites, metal oxides, and reduced metals. Other exemplary materials in particulate and fiber form include apatites, calcium phosphates, aluminosilicates, iron oxides and iron hydroxides, transition metal oxides, and activated carbons. Liquid transfer between particles types can occur, and this transfer can modify the surface and pore properties of each particle type. For example, it is well known that exposure of activated carbon to caustic liquids increases the capacity of the carbon for acid gas interaction, but decreases the efficiency of adsorption of other adsorbates. Those skilled in the art will recognize that materials that carrier liquids containing reactive agents may be incompatible with certain additional particle types. For instance, some absorbent materials that contain carbon dioxide gas will have significant gas concentration losses when mixed with caustic particles such as carbonates and magnesium oxides. Preferred materials include naturally occurring, synthetic, and recycled materials. Suitable materials include insoluble phosphate containing minerals selected from calcium phosphates, iron phosphates, manganese phosphates, aluminum phosphates, magnesium phosphates, silver phosphates, copper phosphates, zinc phosphates, zirconium phosphates, calcium monophosphates, diphosphates, tricalcium phosphates, octaphosphate, metaphosphates, metal oxides selected such as aluminum oxides, iron oxides, magnesium oxides, calcium oxides, manganese oxides, zinc oxides, copper oxides, titanium oxides, silicon oxides, aluminum containing minerals such as alumina bauxite, kaoline, iron containing minerals such as iron oxide, amorphous hydrous ferric oxide, maghemite, hematite, goethite, lepidocrocite, manganese containing minerals such as manganese oxide, pyrolusite, silica containing minerals including silica, quartz, metals such as iron, copper, manganese, silver, gold, platinum, rhodium, zinc, alloys prepared from iron, copper, zinc, carbon, chromium, manganese, nickel, carbonates such as calcium carbonate, magnesium carbonate, iron carbonate, aluminum carbonate, sulfates including magnesium sulfate and calcium sulfate, hydroxides such as aluminum hydroxide, iron hydroxide, magnesium hydroxide, calcium hydroxide, and copper hydroxide.

Synthetic and natural fibers, including strings, yarns and textiles including cotton, wool, polypropylene, rayon, polyester, nylon, acrylic, also are suitable. One preferred material is an ion exchange material, such as resins selected from functionalized styrenes, vinylchlorides, divinyl benzenes, methacrylates, acrylates, or mixtures, copolymers, and blends thereof. Natural and synthetic zeolites such as clinoptilolite and glauconate are preferred.

Catalytic materials generated from these components are quite common and these are applicable in all known forms. The deposition of molecules containing active sites that include metals and atoms and nanocomposites of metals and semimetals on the surface of support materials is immediately applicable.

The particulate and fiber materials may be surface modified with a range of compounds and through different known binding methods. Preferred surface modifications yield cationic surface functionalities. Examples of preferred surface modification chemicals include chemical agents selected from 3-acryloxypropylotrichlorosilane, 3-acrlyoxypropylotrimethocysilane, allyltrichlorosilane, allyltrimethoxysilane, allyltriethoxysilane, 3-bromopropylotrichlorosilane, 3-bromopropyl-trimethoxysilane, (p-chloromethyl)phenyltrichlorosilane), (p-chloromethyl)phenyltrimethoxy-silane, 1-trimethoxysilyl-2-2(p,m-chloromethyl)-phenylethane, chloromethyltrichlorosilane, chloromethyltriethoxysilane, 2-chloroethyltriethoxysilane, 3-chloropropyltrichlorosilane, 3-chloropropyltrimethoxysilane, 3-glycidoxypropyltrimethoxysilane, 3-iodopropyltrimethoxy-silane, 3-isocyanatopropyltriethoxysilane, 2-(diphenylphosphino)ethyltriethoxysilane, vinyltriacetoxysilane, vinyltrichlorosilane, vinyltriethoxysilane, vinyltrimethoxysilane, 3-mercaptopropyltrimethoxysilane, 3-mercaptopropyltriethoxysilane, N(triethoxysilylpropyl)urea, 3-aminopropyl-triethoxysilane, 3-aminopropyltrimethoxysilane, N-(2-aminoethyl)-3-aminopropyltrimethoxysilane, 2-(carbomethoxy)ethyltrichlorosilane, N-[(3 trimethoxysilyl)-propyl]ethylenediamine triacetic acid, trisodium salt, 3-cyanopropyltrichlorosilane, 3-cyanopropyltriethoxysilane, 2-(4-chlorosulfonylphenyl)ethyltrichlorosilane, 2-(4-chlorosulfonylphenyl)ethyltrimethoxysilane, 2-(trimethoxysilyl)ethyl-2-pyridine, N-(3-trimethoxysilylpropyl)pyrrole, N-octadecyldimethyl-1(3-trimethoxysilyl)propyl]ammonium chloride, N-trimethoxysilylpropyl-n,n,n-trimethyl ammonium chloride, 3-(trimethoxysilyl)propyldimethyloctadecylammonium chloride silane quaternary amine, chloropropyl trihydroxy silane, polyamines, polyamides, polyalcohols, polysaacharides, polyacrylamides, polyacrylates, humic acids, peptides, proteins, polorganozirconates, polyorganoaluminates, polysiloxanes, polysilanes, polysilazanes, polycarbosilanes, polyborosilanes, zirconium dimethacrulate, zirconium tetramethacrylate, zirconium 2-ethylhexanoate, aluminum butoxides, aluminum diisopropoxide ethylacetoacetate, tetramethyldisiloxanes and derivatives thereof, tristrimethylsilylphosphate and tristrimethylsiloxyboron, polyamines such as poly(DADMAC), poly-DADM, polyamine-poly(DADMAC) blends, polyquartenary amines, inorganic-polyamine blends, and inorganic poly (DADMAC) blends, cationic starch, cationic poly-methylmethacrylates, copolymers of vinylimidazolium methochloride and vinylpyrrolidone, quartemized vinylpyrrolidone/dimethyl-aminoethyl-methacrylate copolymer, polyethyleneimine, or combinations thereof.

In another embodiment, the surfaces of both the expanding and non-expanding materials are modified by surface binding methods of biological material, proteins, peptides, antibodies, or pharmaceutical agents. Numerous procedures exist in the art for generating stable surface coatings of these materials. Furthermore, the ability to immobilize genetic information as well as proteins and peptides, enables the materials and methods to be used in sensing and sensor development during gas generation, while containing reactive gases, or after the gas has been utilized.

Polycarbonate

In a preferred embodiment, the absorbent material comprises a polycarbonate. It has been observed that polycarbonate has a significant capacity for storing and releasing chlorine dioxide. Polycarbonate can contain concentrations of chlorine dioxide great enough to produce a color in the otherwise clear polycarbonate material. For instance, when exposed to solutions of high concentrations of chlorine dioxide, yellow colored polycarbonate objects are obtained. In preferred embodiments, the gas contained within the carbonate is released over time, rendering the reactive gas available for use in a myriad of applications, many of which are described herein. Release/flushing of the reactive gas and solvent from the polycarbonate can be observed by the loss of color. Polycarbonate is commonly used in the medical and surgical field and to produce eyewear or other objects needing high impact resistance. The unique interaction of polycarbonate with chlorine dioxide facilitates the design and application of high impact objects that possess the capacity to control chemical and biological contaminants at their surface.

Figure 2:
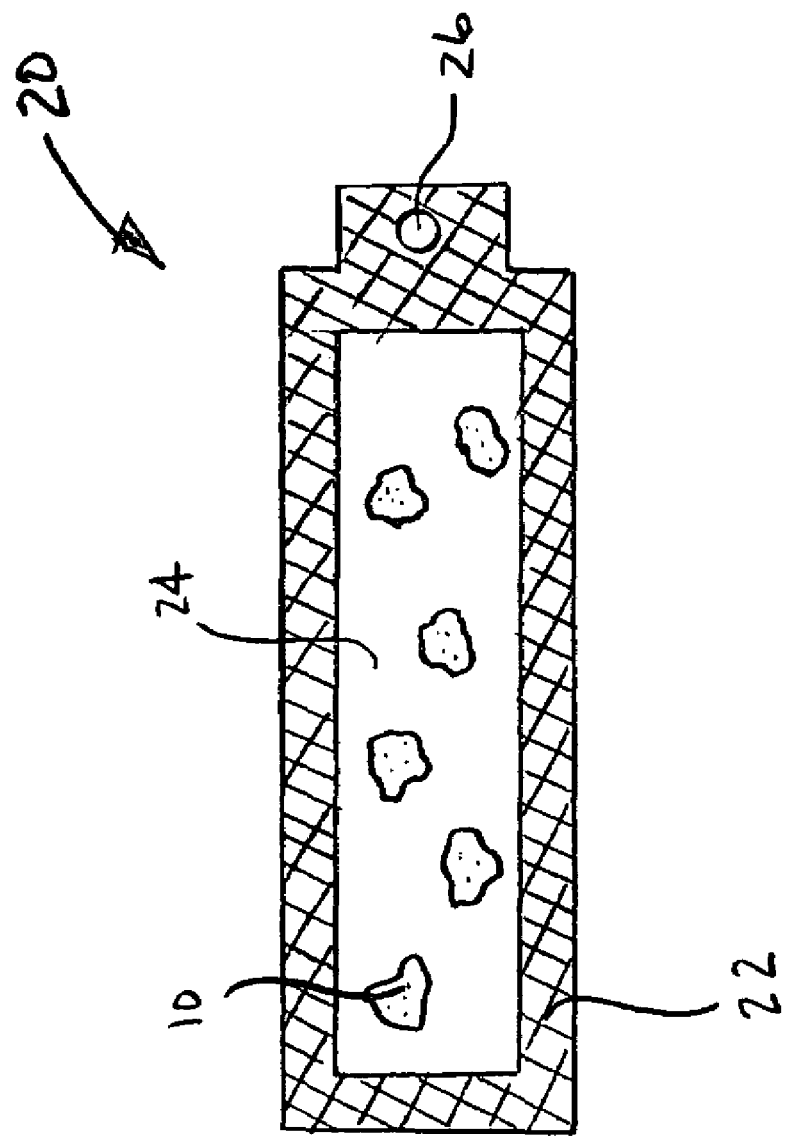
FIG. 2 is a cross-sectional view of one embodiment of an article described herein, which comprises a sachet containing particles for direct release of a gas to an atmosphere or for preparation of a secondary liquid solution.
Figure 3:
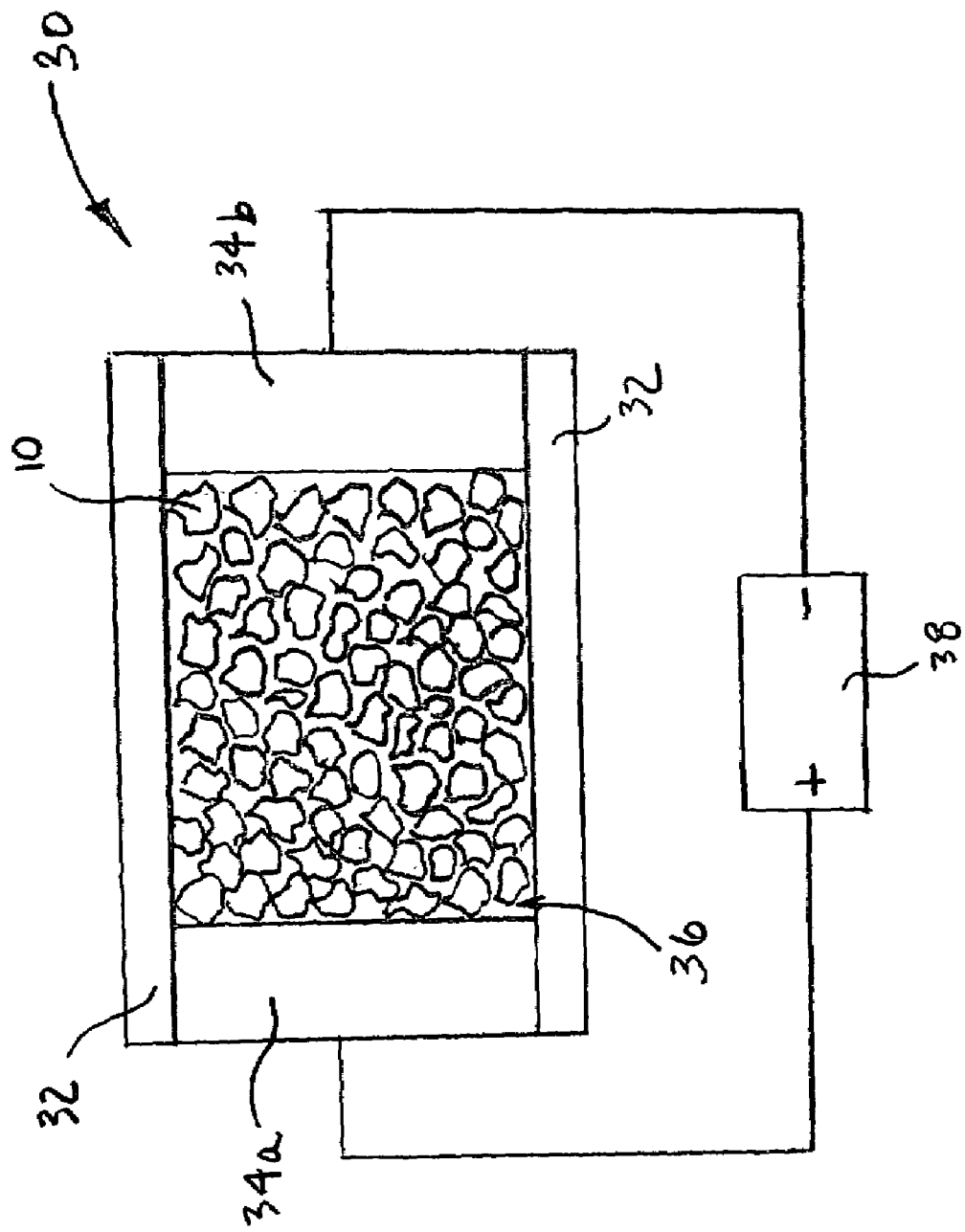
FIG. 3 is a plan view illustrating one embodiment of a device for the electrochemical generation and release of chlorine dioxide.

The structure of certain embodiments of the materials and methods can be understood with reference to FIGS. 1-3, where like parts are numbered the same in each figure. One embodiment of the present compositions and structures is shown in FIG. 1. FIG. 1 illustrates reactive gas containment and release material 10, which comprises (representative) polymer particle 12 in which an aqueous solution 16 of the precursor reagent sodium chlorite and reactive gas chlorine dioxide 14 are absorbed. Reactive particle surface agents 18 are also shown.

FIG. 2 shows an article of manufacture for containing the reactive gas compositions described herein. In particular, FIG. 2 shows a plan, cross-sectional view of a sachet 20 which is comprised of a permeable sachet body 22 having cavity 24 in which particles of a reactive gas containment and release material 10 are contained. The sachet shown includes an optional hole 26 for use in mounting the sachet at a site of reactive gas application.

FIG. 3 shows a device 30 which comprises a small container 32 composed of a gas permeable transparent material. The container houses polymer particles 10 which contain a solution of sodium chlorite. The container includes a transparent window 36 through which particles 10 can be viewed. The container further includes electrodes 34a and 34b, which are connected to a power supply 38. In operation, electric energy from the power source is transmitted through the electrodes and through the polymer particles to electrochemically generate chlorine dioxide, without bulk exchange of liquid to the surrounding atmosphere or liquid. The color of the particles can be viewed for determining the remaining useful lifetime of the particles.

Applications and Uses

The methods and compositions described herein can be adapted to facilitate the use of reactive gases and solutions in a wide variety of applications.

One of the many advantages described herein is the capacity to generate and transfer highly purified chlorine dioxide gas to an application without transfer of bulk reaction liquid, which can contain unreacted precursor reagents, reagents present in excess, or contaminants or reaction byproducts that were initially present in the reaction solution or formed through undesirable reactions. Gas transfer can be completed through atmosphere contact or through the use membranes and porous materials. A number of examples are described herein for the preparation, manipulation, and storage of the materials. The materials prepared are suitable for applications where the reactive gas is used to treat a surrounding atmosphere, transfer a reactive gas to a liquid, and to provide materials suitable for the direct cleaning of surfaces through incorporation in standard cleaning products such as wipes, towels, scrubbers, and handheld tools.

Chlorine Dioxide Utility

Laboratory studies have indicated that chlorine dioxide is an exceptional biocide and highly efficacious at killing bacteria, fungi, molds, algae, protozoa, viruses and cysts. It is excellent in treating biofilms. Chlorine dioxide is useful as a sterilization gas at high concentrations. It is approved by the U.S. Environmental Protection Agency, Food & Drug Agency, and Department of Agriculture for many uses including sterilizing manufacturing and laboratory equipment, bleaching pulp, paper, and textiles, washing fruit and vegetables, disinfecting flume water, disinfecting meat and poultry, disinfecting food processing equipment, sanitizing water, controlling odors in hospitals, petroleum industries, and animal feedlots and rendering operations, treating medical waste, treating municipal water, anthrax decontamination, and cleaning of electronic circuit boards. The gas has been used to treat skin conditions and wounds. Tissue inflammation in some cases may be treated. Chlorine dioxide has significant benefits in the treatment of recreational waters such as in pool and spa water. New applications are being developed rapidly as this strong oxidizer is recognized as being a much safer and more selective reactant than chlorine.

Reactive Gas Applications

Carbon dioxide and sulfur dioxide, as well as inert gases, have significant utility in controlling chemical and biological contamination in liquids, at solid interfaces, and in the local atmosphere around packaged articles.

In one embodiment, the reactive gas methods and materials described herein are used to treat aqueous solutions such as potable water and beverages with chlorine dioxide or another reactive gas such that the liquid obtains a greater degree of purity, through the reduction of biological and chemical contaminants.

In another embodiment, the reactive gas materials and methods are used to treat gaseous systems such as the local atmosphere, enclosed environments, ventilation systems, and breathing air for chemical and biological contaminants and odors.

In a further embodiment, the reactive gas methods and materials are used to treat recreational water systems, such as pools and spas, for chemical and biological contaminants and for preventing biological contamination, as well as in combination with other treatment agents such as corrosion inhibitors, flocculating agents, and water quality enhancers.

In still another embodiment, the reactive gas methods and materials are used in preparing cleaning or decontamination solutions useful for cleaning or decontaminating porous and hard surfaces, such as sensitive surfaces such as circuit boards, electronic equipment and machinery. Advantageously, the present materials and methods enable one to treat a surface with a high concentration of a biocidal gas without transferring a bulk liquid to the surface.

In a further embodiment, the methods and materials are used to create laundry "detergent" formulations that utilize the cleaning properties of one or more reactive gases or solutions.

In one embodiment, the materials and methods are used to sterilize liquid and solid materials associated with hospital, medical, surgical, or dental use. The compositions and methods described herein are used to prepare a material that can treat, through absorption and solidification, biological and medical wastes, as example wastes containing animal fluids. For instance, the materials can be used to control and treat personal fluids found in hospitals and medical situations including blood urine and tissue fluid. The present compositions and material allow simultaneous uptake and solidification (gelling) of these biological fluids, while releasing a strong biocidal gas that diffuses through the container holding these materials. Treatment of these fluids in this manner significantly reduces the hazards associated with contagion transmission.

In yet another embodiment, the materials and methods are adapted for use in the topical treatment of wounds or other skin conditions.

In one embodiment, the materials and methods are used to treat non-aqueous solutions or liquids, such as fuels, that are contaminated with water, biological and chemical components.

In still another embodiment, the materials and methods are used to provide a material that can simultaneously generate a reactive gas and absorb and adsorb a liquid spill or loose powder. Advantageously, this provides for the control of liquid or powder spills, while neutralizing, decontaminating, or sterilizing components of the liquid or powder. This beneficial characteristic of the materials allows the materials to be used in food processing for the containment of meat, poultry, and fish juices. For instance, juice from meat, poultry, and seafood collect at the bottom of conventional packaging trays, but with the present materials, acidic juices could be absorbed by the polymer and contact the precursors for chlorine dioxide, keeping the food dry and generating chlorine dioxide to prevents microbial growth in the fluid and the surface of the food item.

In one embodiment, the materials are used to absorb and neutralize liquids and powders contaminated with chemical and biological warfare agents. For example, the materials can be used to control and treat unknown liquids and powders that are believed to contain biological and chemical agents intended to be used as a weapon or terrorizing agent. The chemicals associated with the neutralization and hydrolysis of chemical weapons are compatible with the materials, and include acids, caustics, ethanolamine, and surfactants. The materials can simultaneously take up the unknown liquid or powder, neutralize it, and provide a safe disposal option.

In one application, materials are provided for temporarily storing reactive gases and which can be used with devices that can be used once and discarded. Examples of such devices include those associated with preparing drinking water, treating odors, and packaging and transporting and storing foods and beverages. Still other applications include using the materials and methods for simultaneously applying a reactive gas and absorbing juices associated with the preparation, delivery, and storage of food and nutritional products. Further applications include providing materials and devices for personal hygiene use such as diapers, incontinence products, and feminine care products.

The materials can be stored in many containers and packages using a wide range of materials, including polymers, glass, and foil coated materials. Exemplary materials include Teflon, Tyvek, polycarbonate, and polyethylene. Porosity and headspace volume affect loss of gas from the particles. Another beneficial characteristic of the materials include the ability to minimize container headspace volume through the volume expansion of some particle types. In effect, a container is filled to capacity by proper ratio of liquid, particles, and precursor reagents. In one embodiment, the materials are used to prepare sachets containing biocidal gases. The sachets can be included with packaged items including food, medical equipment, and artifacts. In one embodiment, the materials described herein include one or more color indicators for visualizing the concentration of the reactive gases, dissolved reagents, and contaminants and for ascertaining the remaining lifetime of the products that incorporate the materials.

In another embodiment, the material relates gas concentration to surrounding temperature and pressure characteristics.

The materials can be formulated with biodegradable materials to help minimize the environment impact after the materials are depleted of reactive gas and reactive gas precursor. Gases such as chlorine dioxide are also soluble in nonaqueous liquids and thus may be extracted and used in other systems allowing the original materials to be recycled.

The devices, systems, and methods described above will be further understood with reference to the following non-limiting examples.

EXAMPLE 1

Generation of $CLO_2$ via Ploymer/Tap-Water Contact

Sodium chlorite, technical grade, was dissolved in tap water and mixed with commercially available polyacrylic acid and polyacrylamide-containing polymer particles. These polymer particles quickly absorbed the sodium chlorite solution. Slowly, over time, a faint chlorine smell was detected from the container of particles and the individual particles obtained a faint green color. The particles containing chlorine dioxide were observed to be stable over a wide temperature range for many weeks. When exposed to the atmosphere, the particles slowly returned to their original clear form.

EXAMPLE 2

Generation of $CLO_2$ via Mixing of Individual Precursor Particles

Sodium chlorite, technical grade, was dissolved in tap water and mixed with absorbent polyacrylic acid and polyacrylamide copolymer particles. The polymer particles absorbed the chlorite solution. Hydrochloric acid, 31%, was added to water and this solution mixed with polyacrylic acid and polyacrylamide copolymer particles. The polymer particles absorbed the acid solution. Subsequently, the two different particle types, sodium chlorite solution particles and the acid solution particles, were mixed homogeneously. Over time, the particles turn different shades of yellow, and a strong chlorine smell can be detected from the container housing the particles. The solution precursor concentration contained by the two particle types directly affects the rate at which the particles generated chlorine dioxide gas and obtained a yellow color.

EXAMPLE 3

Generation of $CLO_2$ via Chlorite Pellet and Acid Solution Containing Particles Sodium chlorite, technical grade, was compressed into a pellet using a small hand press. Hydrochloric acid, 31%, was added to water and the subsequent solution absorbed into polyacrylic acid and polyacrylamide copolymer particles. The pellet containing sodium chlorite was placed into contact with the acid solution containing particles. The polymer particles in direct contact with the sodium chlorite pellet immediately turned brown in color, while particles not in direct contact with the pellet slowly obtained various shades of yellow. After complete dissolution of the sodium chlorite pellet, all particles obtained the same shade of yellow, indicating diffusion of the chlorine dioxide gas throughout the polymer particles.

EXAMPLE 4

Generation of $CLO_2$ via Direct Acid Injection to Chlorite Particles

Sodium chlorite, technical grade, was mixed with polyacrylic acid and polyacrylamide copolymer particles and placed in a container. A hydrochloric acid solution was introduced directly onto the polymer particles containing the chlorite solution and the container was sealed. The introduced acid solution was immediately absorbed by the particles and golden brown colored particles were generated. A strong chlorine smell was observed from the container. Introduction of several golden brown particles to a small volume of water, generated a bright yellow solution and the polymer particles became colorless. This solution was capable of rapidly removing the blue color from iodine soaked paper.

EXAMPLE 5

Packaging of $CLO_2$ Containing Particles

The chlorine dioxide containing particles described in Examples 1-4 were vacuum packaged using a commercially available household food vacuum sealing equipment. All particle types and solution concentrations could be packaged. Particles containing high enough concentrations of chlorine dioxide to yield yellow colors were observed to be stable in these packages for many weeks.

EXAMPLE 6

Packaging of $CLO_2$ Containing Particles with Tyvek Membrane Materials

The chlorine dioxide containing particles described in Examples 1-4 were placed in sachet type containers prepared with tyvek membrane material and a nonporous polyethylene sheet. This sachet was subsequently vacuum packaged using commercially available household food sealing equipment. Particle color observed by eye through the non-tyvek material indicated no color change over many weeks. Exposure of the sachet to the atmosphere eventually yielded white and then clear particle forms.

EXAMPLE 7

Generation of $CLO_2$ via Exposure to Acid Gas

Sodium chlorite solutions were prepared with tap water and absorbed into polyacrylic acid and polyacrylamide copolymer particles. The particles were exposed to acetic acid vapors, using vinegar as a source. The sodium chlorite polymer particles turned greenish yellow in color after exposure to the acetic acid fumes indicating that the polymer particles have the ability to absorb acid gases and that the chlorite present was available for the generation of chlorine dioxide gas. The polymer particles were observed to be stable and retain color in the acetic acid atmosphere for many months.

EXAMPLE 8

Gas Phase Chlorine Reaction to Generation $CLO_2$ in Particles

Sodium chlorite solutions were prepared with tap water and absorbed into polyacrylic acid and polyacrylamide copolymer particles. The particles were exposed to the chlorine gas using an acidified hypochlorite solution (bleach) as a source. The sodium chlorite polymer particles turned greenish yellow in color indicating that the chlorine gas could be absorbed by the particles and that the chlorite present in the polymer particles was available for chlorine dioxide gas generation. The particles were stable and retained their color in the chlorine gas atmosphere for many months.

EXAMPLE 9

Direct Loading of $CLO_2$ Gas into Particles

Tap water was absorbed into polyacrylic acid and polyacrylamide copolymer particles. The particles were then exposed to chlorine dioxide vapors, generated in a separate container, by the reaction of aqueous solutions of sodium chlorite and hydrochloric acid. The polymer particles became yellow in color indicating chlorine dioxide gas solubility in the particles. Particles were stable for many months.

EXAMPLE 10

Delivery of $CLO_2$ and Uptake of Heavy Metals

Chlorine dioxide gas containing particles prepared in Example 4 were transferred into a small volume of aqueous solution containing copper ion. Upon transfer of the particles, the solution turned yellowish green. Additionally, the polymer particles turned green-blue in color indicating adsorption of copper ions by the polymer. This example provides an example of simultaneous gas delivery to a solution and heavy metal uptake by the polymer. This material characteristic is beneficial in many water treatment and purification applications.

EXAMPLE 11

$CLO_2$ Precursor Storage and Boric Acid

Sodium chlorite solution was absorbed into dry sodium hydroxide containing polyacrylic and polyacrylamide containing polymer particles. The hydroxide containing particles were previously prepared by absorbing a concentrated sodium hydroxide solution and drying. The solution pH of the chlorite containing particles was highly alkaline (pH>10). The particles were then placed in a sealed plastic bag. The particles were stable and uncolored. When several particles were exposed to tap water acidified with boric acid, the solution immediately became yellow in color.

EXAMPLE 12

Electrochemical Generation oh $CLO_2$

A sodium chlorite particulate material was prepared with tap water and polyacrylic acid particles and polyacrylamide copolymer particles. The particles were then placed in a single container that also contained two platinum electrodes connected to a DC power source (type C battery). Shortly after connecting the power supply, the polymer particles became green-yellow in color and a chlorine odor was detected above the container. This example indicates that the polymer particles containing solutions of chlorite can undergo direct electrochemical reaction to produce chlorine dioxide gas, which is both retained and released by the polymer particles. Those skilled in the art of electrochemical devices will understand that AC, solar, or other power sources are likewise suitable for use with the materials.

EXAMPLE 13

Secondary Solution Preparation

A solution of chlorine dioxide was prepared by mixing hydrochloric acid with sodium chlorite in tap water. After formation of a yellow colored solution with a strong chlorine odor, polyacrylic acid and polyacrylamide copolymer particles were introduced. The particles rapidly absorbed the solution containing dissolved chlorine dioxide gas. The particles were stable and retained the yellow color for many weeks. When 5-10 individual particles were transferred to a one liter container of water, the chlorine dioxide concentration was determined to be approximately 1 ppm, using a DPD chlorine test kit.

EXAMPLE 14

Polycarbonate Storage Materials

A solution of chlorine dioxide, yellow in color, was prepared by mixing aqueous solutions of chlorite and hydrochloric acid. This solution was used to fill a transparent polycarbonate container. The container was sealed and stored for several days. After removing the chlorine dioxide solution, the polycarbonate container retained a yellow color. The empty container was placed in a refrigerator with an unpleasant odor. After several minutes the unpleasant odor was no longer detected. The polycarbonate container slowly lost all yellow color over a period of weeks when exposed to the atmosphere.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

I claim:

1. A composition for use in containing and releasing a reactive gas comprising:
   a reactive gas, reactive gas precursor, or combination thereof, wherein the reactive gas precursor comprises an oxidizing agent selected from the group consisting of hypochlorite, hypochlorous acid, ozone, peroxide, and monopersulfate;
   a fluid in which the reactive gas, reactive gas precursor, or combination thereof is dissolved; and
   a solid material in which the fluid is absorbed or adsorbed, wherein the solid material controls the formation or release of the reactive gas.

2. A composition for use in containing and releasing a reactive gas comprising:
   a reactive gas, reactive gas precursor, or combination thereof;
   a fluid in which the reactive gas, reactive gas precursor, or combination thereof is dissolved, wherein the fluid comprises a non-polar liquid; and
   a solid material in which fluid is absorbed or adsorbed, wherein the solid material controls the formation or release of the reactive gas.

3. A composition for use in containing and releasing a reactive gas comprising:
   a reactive gas, reactive gas precursor, or combination thereof;
   a fluid in which the reactive gas, reactive gas precursor, or combination thereof is dissolved;
   a first solid material in which the fluid is absorbed or adsorbed; and
   a second solid material in which an acid is absorbed, wherein the first or second solid material comprises an acid polymer selected from the group consisting of polylactic acids, polyglycolic acids, polyacrylic acids, polyacrylamides, polyesters, polyhydroxls, polyalcohols, polyanhydrides, and gums, wherein the combination of the first and second solid materials controls the formation and release of the reactive gas.

4. A composition for use in containing and releasing a reactive gas comprising:
   a reactive gas, reactive gas precursor, or combination thereof;
   a fluid in which the reactive gas, reactive gas precursor, or combination thereof is dissolved; and
   a solid material, which comprises a polycarbonate, in which the fluid is absorbed or adsorbed,
   wherein the solid material controls the formation or release of the reactive gas.

5. A composition for use in containing and releasing chlorine dioxide gas comprising:
   a liquid solution of a chlorate salt, a chlorite salt, chlorine dioxide, or a combination thereof;
   first polymeric particles or fibers in which the liquid solution is absorbed or adsorbed; and
   second polymeric particles or fibers, which comprise a polyacid, combined with the first polymeric particles or fibers,
   wherein the combination of the first and second polymeric particles or fibers controls the formation and release of chlorine dioxide.

6. A composition for use in containing and releasing chlorine dioxide gas comprising:
   a liquid solution of a chlorate salt, a chlorite salt, chlorine dioxide, or a combination thereof; and
   polymeric particles or fibers, which comprise an acid polymer,
   wherein the liquid solution is absorbed in the polymeric particles or fibers and the polymeric particles or fibers control the release of chlorine dioxide.

7. An apparatus for use in containing and releasing a reactive gas comprising:
   a composition which comprises (i) a reactive gas, reactive gas precursor, or combination thereof, (ii) a fluid in which the reactive gas, reactive gas precursor, or combination thereof is dissolved, and (iii) a solid material in which fluid is absorbed or adsorbed, wherein the solid material controls the formation or release of the reactive gas;
   a container having an enclosed cavity in which the composition is disposed; and
   at least a pair of electrodes connected to a power source, the electrodes being positioned to pass an electric current or voltage through the composition.

8. A method of making a composition for the containment and release of a reactive gas comprising:
   dissolving a first reactive gas precursor in a fluid to form a solution;
   absorbing or adsorbing the solution in an absorbent solid material; and
   exposing the solid material to a gaseous second reactive gas precursor to generate a reactive gas in the solid material, which is substantially non-reactive with the reactive gas, the fluid, or the reactive gas precursors.

9. The method of claim 8, wherein the gaseous second reactive gas precursor is an acidic, oxidizing, or reducing gas.

10. The method of claim 8, wherein the solid material is in the form of particles or fibers.

11. The method of claim 8, wherein the reactive gas is selected from the group consisting of chlorine dioxide, chlorine, bromine, iodine, carbon dioxide, oxygen, nitrogen, sulfur dioxide, hydrogen sulfide, hydrogen cyanide, chlorine monoxide, nitrogen monoxide, and nitrogen dioxide.

12. The composition of claim 5, wherein the second polymeric particles further comprise an absorbed or adsorbed liquid acid.

* * * * *